(12) United States Patent
Huang et al.

(10) Patent No.: US 11,586,302 B2
(45) Date of Patent: Feb. 21, 2023

(54) PRESSABLE TOUCH PANEL AND ULTRASOUND IMAGING SYSTEM

(71) Applicant: GE Precision Healthcare LLC, Wauwatosa, WI (US)

(72) Inventors: Fenggui Huang, Wauwatosa, WI (US); Yalan Yang, Wauwatosa, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 304 days.

(21) Appl. No.: 17/141,712

(22) Filed: Jan. 5, 2021

(65) Prior Publication Data
US 2021/0204913 A1 Jul. 8, 2021

(30) Foreign Application Priority Data
Jan. 7, 2020 (CN) .......................... 202010014374.4

(51) Int. Cl.
| G06F 3/041 | (2006.01) |
| G06F 3/0354 | (2013.01) |
| A61B 8/00 | (2006.01) |

(52) U.S. Cl.
CPC .......... *G06F 3/03547* (2013.01); *A61B 8/467* (2013.01); *G06F 3/041* (2013.01); *G06F 2203/04105* (2013.01)

(58) Field of Classification Search
CPC ......... A61B 8/467; A61B 8/4427; A61B 8/54; A61B 8/44; A61B 8/4405; A61B 8/4416; A61B 8/4444; A61B 8/485; A61B 8/488; G06F 3/041; G06F 2203/04105; G06F 3/0414; G16H 40/63
See application file for complete search history.

(56) References Cited

U.S. PATENT DOCUMENTS

| 9,477,328 B2 | 10/2016 | Clayton | |
| 10,282,025 B2 | 5/2019 | Mickelsen | |
| 2004/0002356 A1* | 1/2004 | Honda | G06F 3/0338 |
| | | | 455/575.1 |
| 2009/0135145 A1* | 5/2009 | Chen | G06F 3/016 |
| | | | 345/173 |
| 2012/0182236 A1* | 7/2012 | Tsai | G06F 1/169 |
| | | | 345/173 |
| 2015/0008113 A1* | 1/2015 | Liu | H01H 13/14 |
| | | | 200/515 |
| 2017/0038801 A1* | 2/2017 | Lee | G06F 3/041 |
| 2018/0004342 A1* | 1/2018 | Lee | G06F 3/044 |
| 2018/0278288 A1* | 9/2018 | Yamaguchi | G06F 1/1656 |
| 2019/0336101 A1* | 11/2019 | Chiang | A61B 1/00 |

FOREIGN PATENT DOCUMENTS

KR   1013246311 B1   11/2013

* cited by examiner

*Primary Examiner* — Michael J Jansen, II
*Assistant Examiner* — Sosina Abebe

(57) ABSTRACT

Provided in the present application are a pressable touch panel and an ultrasound imaging system. The pressable touch panel includes a touch assembly, an elastic member and a housing. The touch assembly includes a first surface for receiving a touch force, the elastic member is arranged below the touch assembly, and the housing is used to accommodate the elastic member, wherein the elastic member is confined by the housing to be in a compressed state to prevent liquid from passing through the elastic member.

9 Claims, 10 Drawing Sheets

PRESSABLE TOUCH PANEL AND ULTRASOUND IMAGING SYSTEM

TECHNICAL FIELD

The present invention relates to the field of ultrasonic detection, and more particularly to a pressable touch panel and an ultrasound imaging system.

BACKGROUND

Ultrasonic detection is a common detection method in the modern medical field. An ultrasound system has a control panel with many user controls for setting up and controlling the system to perform the desired imaging examination.

A user can set an imaging mode based on a control panel. For example, an operator can set an imaging mode for B-mode, Doppler or M-mode; or change the size and angle of an image field, and adjust the frequency for fundamental or harmonic imaging; or adjust the system gain to more clearly distinguish deeper anatomical structures in the human body, and adjust time gain control slides to provide the appropriate gain at the depth of interest; or add focal zones and reposition the focal zones to different depths, for example, a spectral Doppler display when a Doppler gate is placed on an anatomical structure; or form a variety of measurement results from estimated anatomical structures and blood flow parameters. These operations are only some of the controls and adjustments available on a control panel of a typical ultrasound system.

Although each ultrasonic examination can require the adjustment and use of many controls on the above control panel, different types of examinations can require the use of a slightly or significantly different group of controls. Therefore, the control panel must contain a very large number of user controls to accommodate all the variable uses and functions of the ultrasound system. The ever-increasing number of controls has been addressed by different equipment providers in different ways. Some solutions are to simply increase the number and/or density of mechanical controls on the control panel. Other solutions are to augment the mechanical controls with softkey controls on a display screen of the system, and the user can call up, adjust and click the controls on the control panel with a computer mouse or a trackball. Still other solutions have employed softkey controls on a touch panel display, and the user can manipulate and adjust manually the softkey controls without the need for a computer pointing device.

Conventionally, the control panel is provided with a trackball, and the user (for example, a sonographer) manipulates the trackball to indicate an anatomical structure of an ultrasound image on an image display, and manipulates a cursor or pointer on the screen to indicate a softkey on the display screen, which is selected by clicking a button adjacent to the trackball.

In the ultrasound imaging system, the conventional trackball is replaced with a touch panel to make the operation more convenient. However, the touch panel cannot be pressed, which will limit the function of the touch panel and complicate the operation process.

SUMMARY

Provided in the present invention is a pressable touch panel comprising a touch assembly, an elastic member and a housing. The touch assembly comprises a first surface for receiving a touch force, the elastic member is arranged below the touch assembly, and the housing is used to accommodate the elastic member, wherein the elastic member is confined by the housing to be in a compressed state to prevent liquid from passing through the elastic member.

Optionally, the housing comprises a base arranged below the elastic member and a side portion connected to the base, and the side portion is used to confine the elastic member such that the elastic member is in a compressed state.

Optionally, the base is used to conduct the heat generated by a controller mounted below the touch panel to the elastic member so as to evaporate residual liquid on the elastic member.

Optionally, the ultrasound imaging system comprises a mounting housing for arranging the touch panel, and the side portion of the housing of the touch panel is provided with a sealing member extending to the mounting housing to block and prevent liquid from entering a gap between the mounting housing and the side portion of the housing of the touch panel.

Optionally, the side portion is provided with a connecting member mating with the base to connect the base.

Optionally, the touch assembly comprises a pressing board, a cover board and a circuit board sequentially arranged from top to bottom, and an upper surface of the pressing board is the first surface.

Optionally, the touch assembly further comprises a switch member and a connector arranged on a lower surface of the circuit board, and the switch member is used to transmit a touch signal to the circuit board through the connector under the action of the touch force.

Optionally, the elastic member comprises a cap-shaped body comprising: a cap top that contacts at least one of the circuit board and the switch member, an outer edge portion that contacts the base, and an inclined side portion connected to the cap top and the outer edge portion.

Optionally, at least one second opening is arranged on a portion of the cap top that does not contact the switch member.

Optionally, the cap top of the cap-shaped body comprises a first opening, the elastic member further comprises a bowl-shaped structure arranged in the first opening, a protrusion is arranged on a bottom surface of the bowl-shaped structure and contacts the switch member, and a space is formed between an inner side surface of the bowl-shaped structure and the protrusion.

Provided in an exemplary embodiment of the present invention is an ultrasound imaging system comprising the above pressable touch panel.

Other features and aspects will become clear through the following detailed description, accompanying drawings and claims.

BRIEF DESCRIPTION OF THE DRAWINGS

The present invention may be better understood by describing exemplary embodiments of the present invention with reference to accompanying drawings, in which.

DETAILED DESCRIPTION OF THE EMBODIMENTS

Specific implementations of the present invention will be described in the following. It should be noted that during the specific description of the implementations, it is impossible to describe all features of the actual implementations in detail in this description for the sake of brief description. It should be understood that in the actual implementation of any of the implementations, as in the process of any engineering project or design project, a variety of specific decisions are often made in order to achieve the developer's specific objectives and meet system-related or business-related restrictions, which will vary from one implementation to another.

Moreover, it can also be understood that although the efforts made in such development process may be complex and lengthy, for those of ordinary skill in the art related to content disclosed in the present invention, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art to which the present invention pertains. The words "first," "second," and similar words used in the description and claims of the patent application of the present invention do not denote any order, quantity or importance, but are merely intended to distinguish between different constituents. "One," "a(n)" and similar words are not meant to be limiting, but rather denote the presence of at least one. The word "include," "comprise" or a similar word is intended to mean that an element or article that appears before "include" or "comprise" encompasses an element or article and equivalent elements that are listed after "include" or "comprise," and does not exclude other elements or articles. The word "connect," "connected" or a similar word is not limited to a physical or mechanical connection, and is not limited to a direct or indirect connection.

Figure 1:
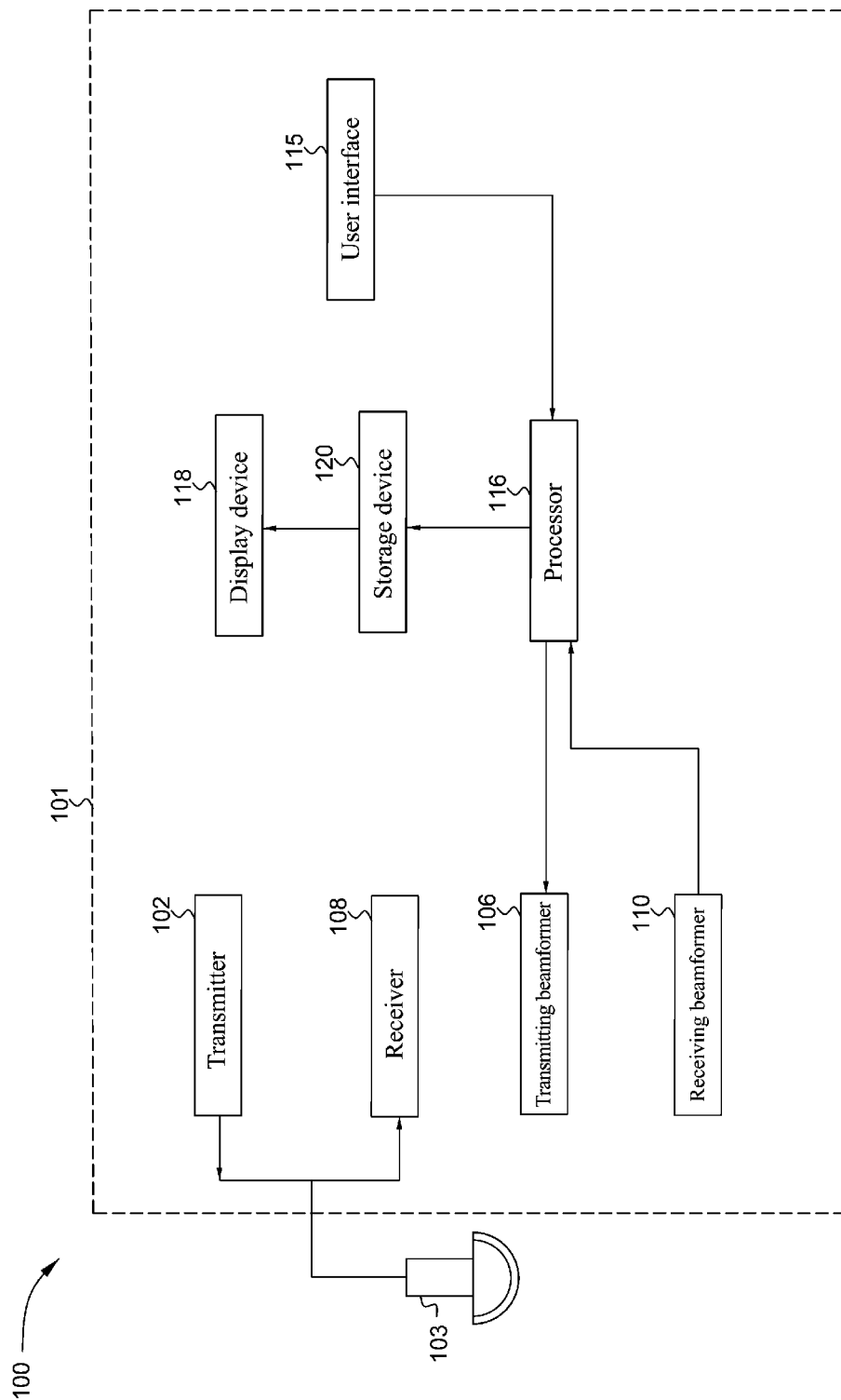
FIG. 1 is a schematic diagram of an ultrasound imaging system according to some embodiments of the present invention.

FIG. 1 shows an ultrasound imaging system 100 according to some embodiments of the present invention. As shown in FIG. 1, the ultrasound imaging system 100 comprises an ultrasound imaging apparatus 101 and a probe 103. The ultrasound imaging apparatus 101 may have different sizes and/or shapes. For example, the ultrasound imaging apparatus may be a cart-based ultrasound imaging apparatus, or a laptop computer-type ultrasound imaging apparatus, or a handheld ultrasound imaging apparatus.

The ultrasound imaging apparatus 101 includes a transmitting beamformer 106, a transmitter 102, a receiver 108 and a receiving beamformer 110. The transmitting beamformer 106 and the transmitter 102 drive (an internal element, e.g. a piezoelectric element, of) the probe 103 to transmit a pulsed ultrasound signal to an object under detection (not shown). The pulsed ultrasound signal is backscattered from a structure (like blood cells or muscle tissue) in the body to generate an echo that returns to the probe 103. The echo is converted into an electrical signal or ultrasound data by the probe 103, and the receiver 108 receives the electrical signal. The electrical signal representing the received echo passes through the receiving beamformer 110 that outputs ultrasound data.

According to some embodiments, the probe 103 may comprise an electronic circuit system to perform all or part of the transmitting and/or receiving beamforming. For example, all or part of the transmitting beamformer 106, the transmitter 102, the receiver 108 and the receiving beamformer 110 may be located in the probe 103. In addition, the probe 103 may be either a 2D array probe, or a 3D or 4D array probe. The term "scan or scanning" may also be used to refer to the acquisition of data in the process of transmitting and receiving ultrasound signals. The term "data" or "ultrasound data" may be used to refer to one or more data sets acquired by an ultrasound imaging system.

The ultrasound imaging apparatus 100 further includes a processor 116 to control the transmitting beamformer 106, the transmitter 102, the receiver 108 and the receiving beamformer 110. The processor 116 is communicatively connected to the probe 103. Specifically, the processor 116 can control the shape of the beam emitted from the probe 106, acquire data from the probe 103, process the acquired ultrasound information (e.g. RF signal data or IQ data pairs), and prepare a frame of the ultrasound information for display on a display device 118. The term "communicatively connected" includes wired and wireless connection. In some embodiments, the processor 116 may also include a complex demodulator (not shown) that demodulates RF data and generates raw data.

Specifically, the processor 116 may include a central processing unit (CPU). Optionally, the processor 116 may include other electronic components capable of executing processing functions, such as digital signal processors, field programmable gate arrays (FPGA) or graphic boards. In some embodiments, the processor 116 may include multiple electronic components capable of executing processing functions. For example, the processor 116 may include two or more electronic components selected from an electronic component list including a central processing unit, a digital signal processor, a field programmable gate array and a graphic board.

The ultrasound imaging apparatus 100 further includes a display device 118. The display device 118 includes one or more monitors that display patient information including diagnostic ultrasound images to the user for diagnosis and analysis. The display device 118 is communicatively connected to the processor 116.

The ultrasound imaging apparatus 100 further includes a storage device 120 for storing the acquired data (or data sets) and/or images. For example, the storage device 120 may include a hard disk drive, a floppy disk drive, a CD-read/write (CD-R/W) drive, a digital versatile disc (DVD) drive, a flash drive and/or a solid-state storage device.

The ultrasound imaging apparatus 100 further includes a user interface 115. The user interface 115 can be used to control the operation of the ultrasound imaging system 100, including controlling the input of patient data, changing scan or display parameters, etc. The user interface 115 may include a mouse, a keyboard, a voice activated controller, or a form of an operator interface of any other suitable input device, etc.

In various embodiments of the present invention, data can be processed by other or different mode-related modules of the processor 116 (for example, B-mode, color Doppler, M-mode, color M-mode, spectral Doppler, elastography, tissue velocity imaging (TVI), strain imaging, strain rate imaging, etc.) to form 2D or 3D or 4D data. For example, one or a plurality of modules can generate B-mode, color Doppler, M-mode, color M-mode, spectral Doppler, elastography, TVI, strain imaging, strain rate imaging and combinations thereof, etc.

It should be noted that various embodiments can be described in conjunction with an ultrasound system, but methods and systems are not limited to ultrasound imaging or its specific configuration. Various embodiments can be implemented in conjunction with different types of imaging systems, including, for example, multi-modality imaging systems having ultrasound imaging systems and one of x-ray imaging systems, magnetic resonance imaging (MM) systems, computed tomography (CT) imaging systems, positron emission tomography (PET) imaging systems, among others. In addition, various embodiments can be implemented in non-medical imaging systems, for example, non-destructive detection systems such as ultrasound weld detection systems or airport baggage scanning systems.

Figure 2:
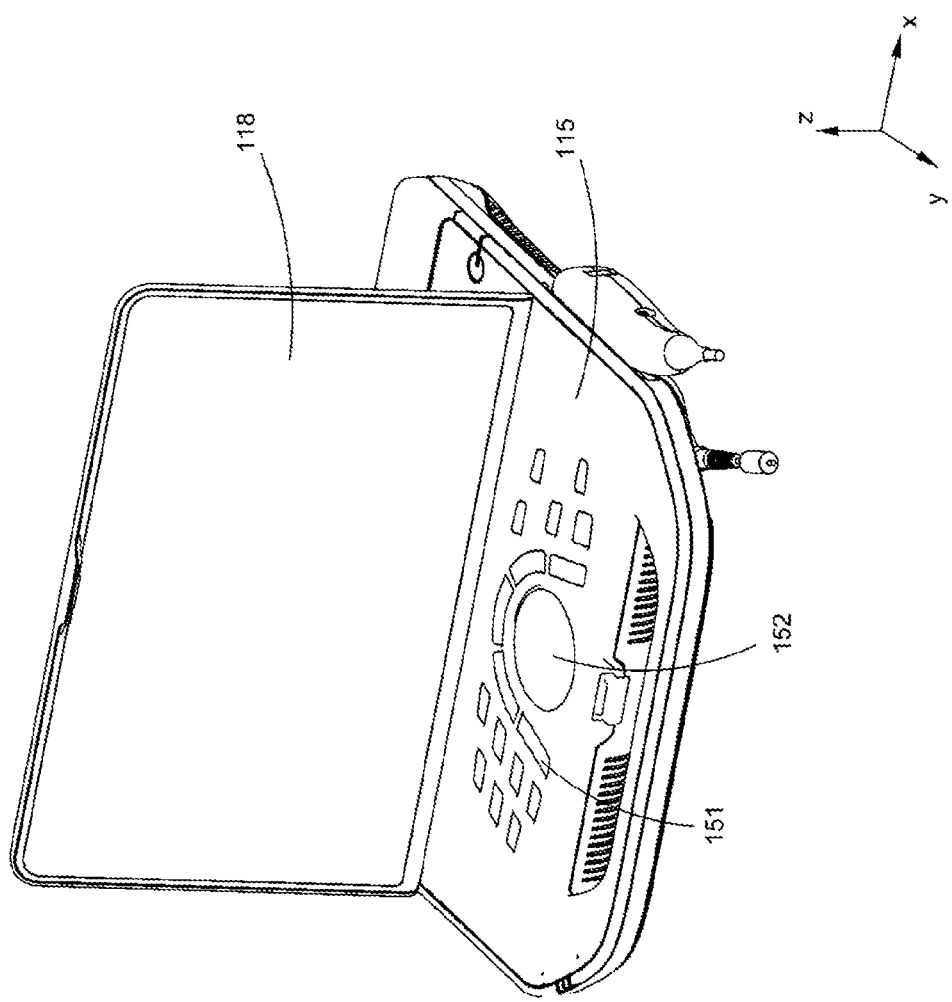
FIG. 2 is a schematic diagram of a user interface in the ultrasound imaging system shown in FIG. 1.

FIG. 2 shows the user interface 115 in the ultrasound imaging system 100 shown in FIG. 1. As shown in FIG. 2, the user interface 115 includes a control button 151 and a pressable touch panel 152. The control button 151 can be used to control the ultrasound imaging system as desired or needed and/or as typically provided. The user can physically manipulate the pressable touch panel 152 to interact with ultrasound data and other data that may be displayed, and to input information and set and change scanning parameters and viewing angles, etc. For ease of description, the lengthwise direction parallel to the display device 118 is defined as an x-axis direction, the direction perpendicular to the x-axis direction in the plane where the pressable touch panel 152 is located is defined as a y-axis direction, and the direction perpendicular to the plane where the pressable touch panel 152 is located is defined as a z-axis direction.

Although the pressable touch panel described in the present invention is implemented based on the ultrasound imaging system, those skilled in the art should understand that the pressable touch panel of the present invention is not limited to be applied to ultrasound imaging systems, and can also be applied to notebook computers, or industrial computers (or industrial control computers), or other machines or equipment in medical industry to solve the technical problem that touch panels on the industrial control computers cannot be pressed at all positions, so that the touch panels can be pressed at any position, without being limited to a specific area or position.

In addition, since the trackball of the ultrasound imaging system is replaced with the pressable touch panel, and since the user (for example, a sonographer) wants the system to give feedback when pressing the touch panel, to confirm the success of the pressing, the pressable touch panel of the present invention can be provided with the elastic member to provide a first position in a normal state and a second position in a pressed state. A gap is formed between the touch panel and the housing (such as the mounting housing of the touch panel) due to the displacement of the touch panel in the direction of the pressing force, which causes liquid (for example, a disinfectant) to flow into the touch panel through the gap when the ultrasound imaging system is cleaned or disinfected; and a master controller or a host computer of the ultrasound imaging system is mounted below the touch panel, and hence may be damaged by liquid entering the master controller or the host computer.

Figure 3:
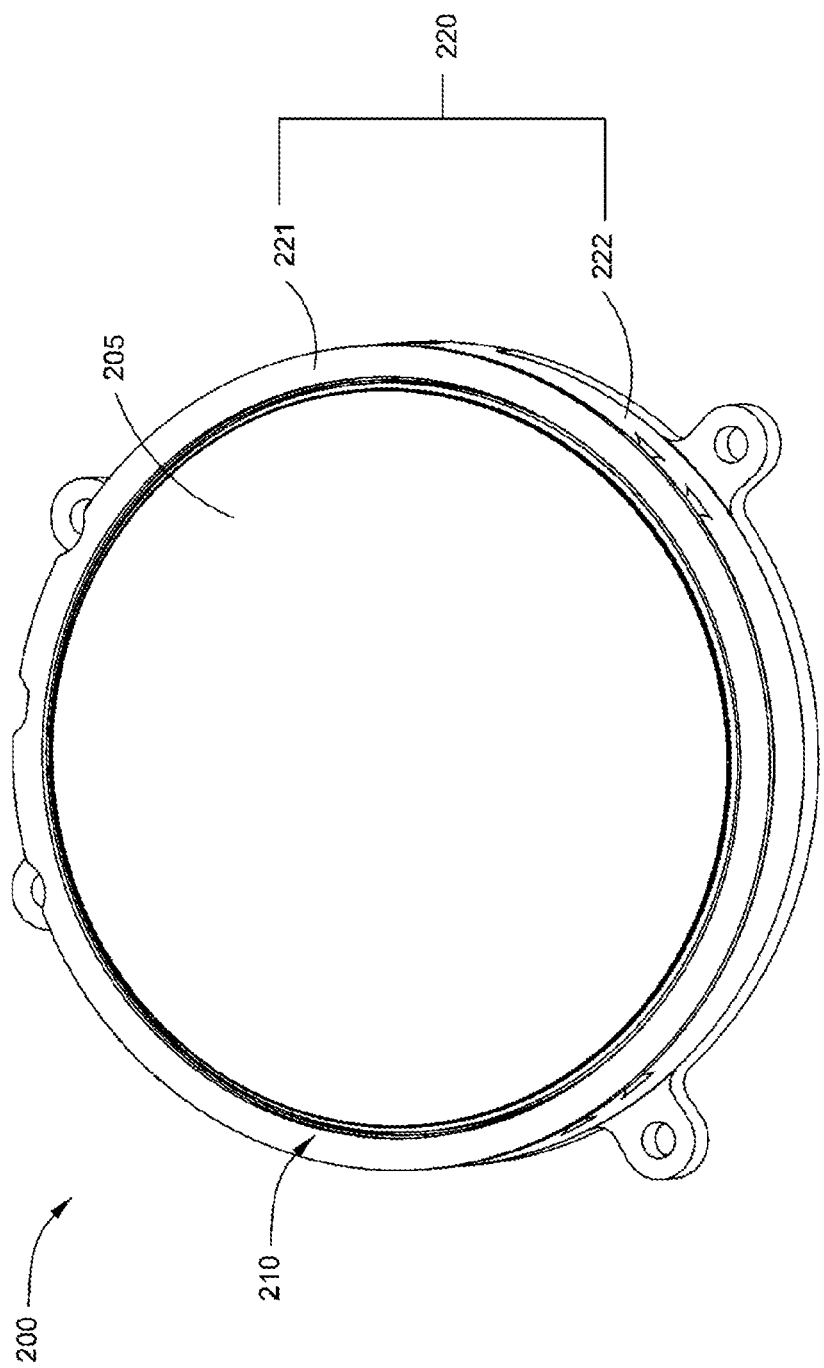
FIG. 3 is a perspective view of a pressable touch panel in the user interface shown in FIG. 2 in a first direction.
Figure 4:
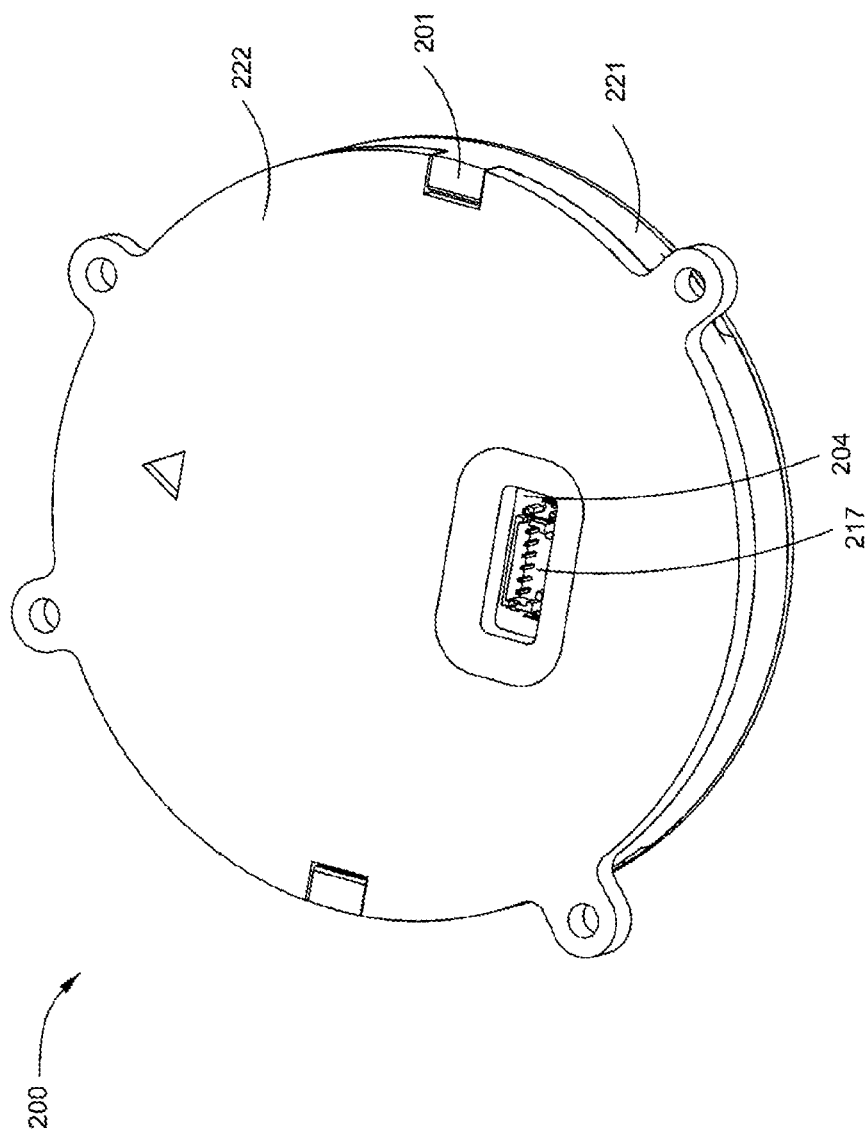
FIG. 4 is a perspective view of the pressable touch panel shown in FIG. 3 in a second direction.
Figure 5:
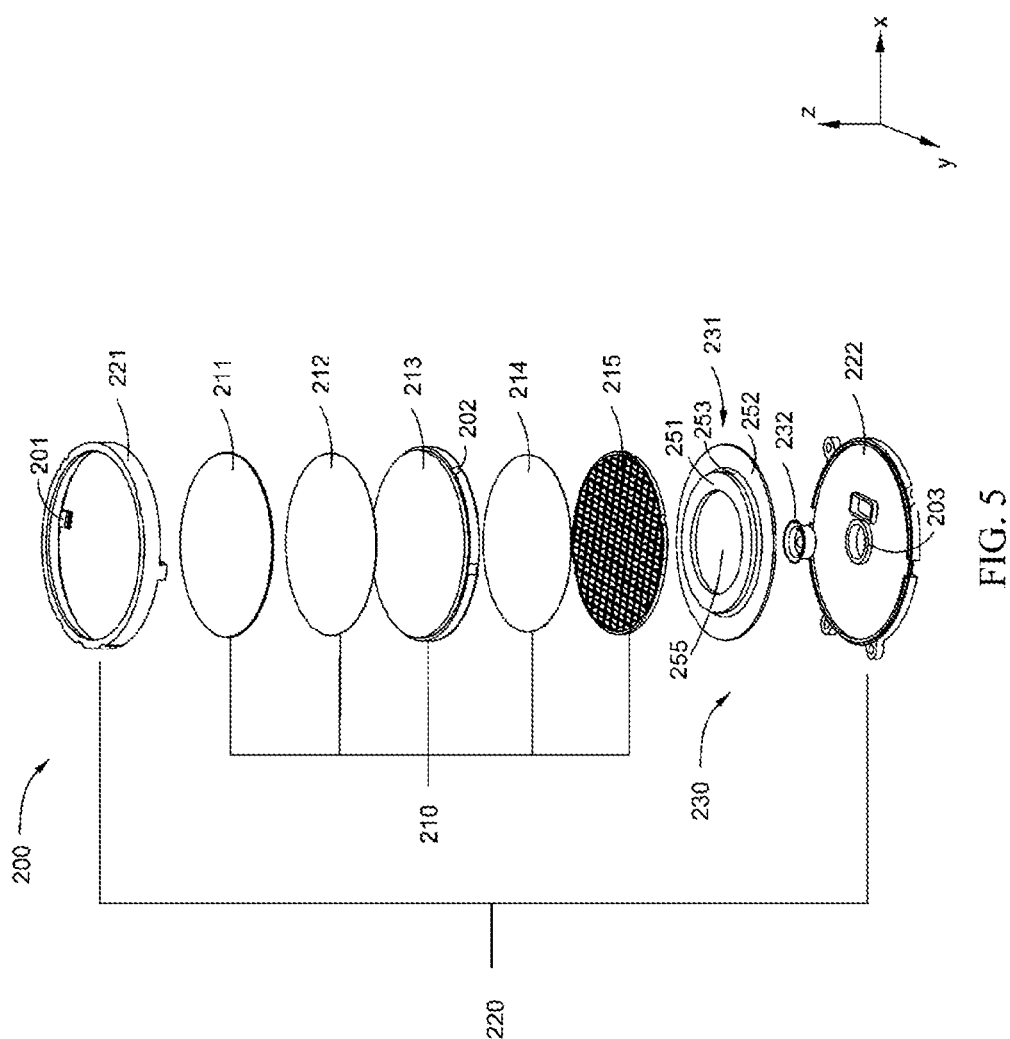
FIG. 5 is an exploded diagram of a pressable touch panel according to some embodiments of the present invention.
Figure 6:
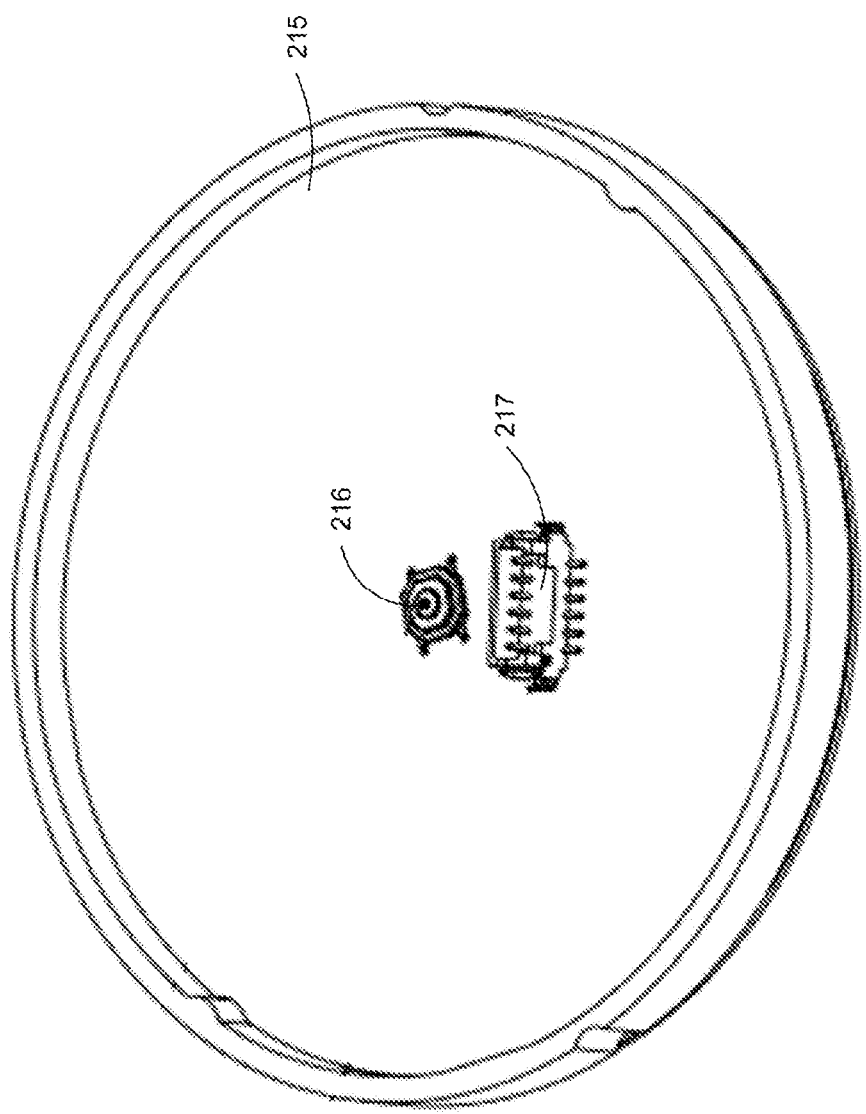
FIG. 6 is a bottom view of a circuit board in the pressable touch panel shown in FIG. 5
Figure 7:
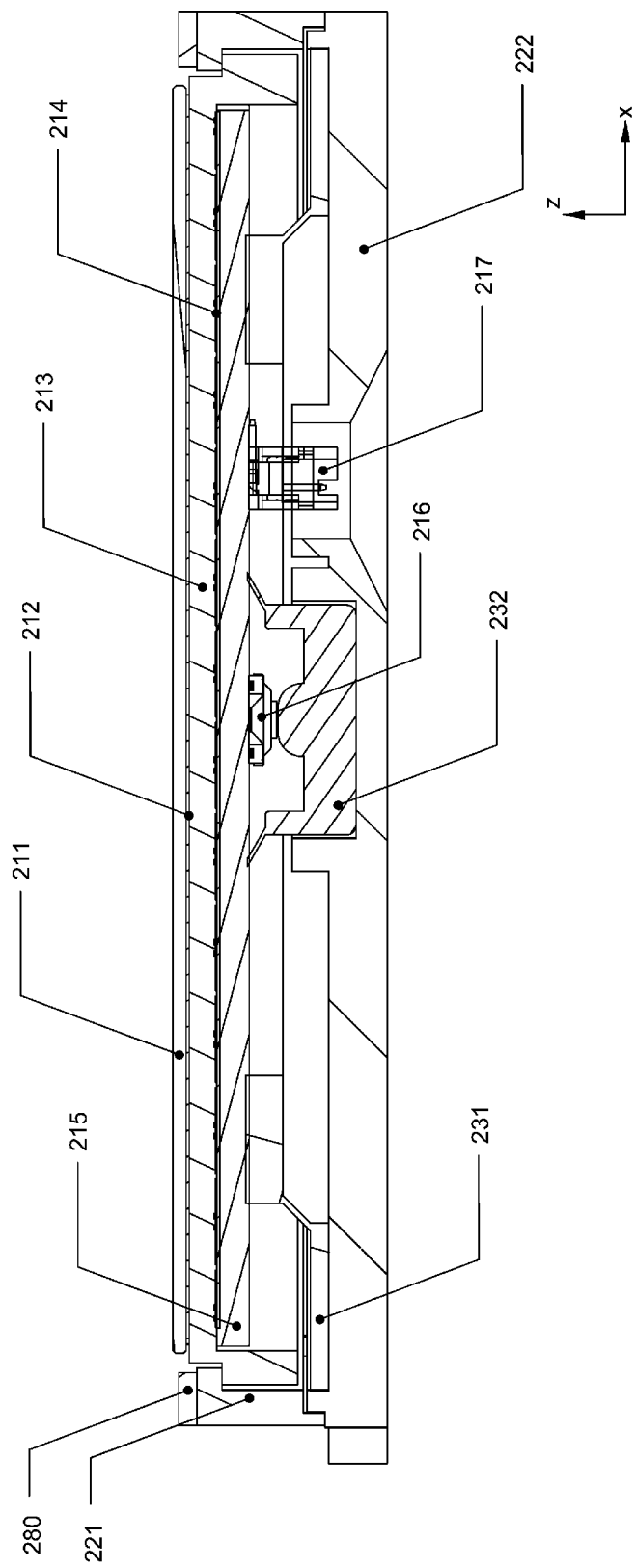
FIG. 7 is a sectional view of the pressable touch panel shown in FIG. 5 in an A-A direction.
Figure 8:
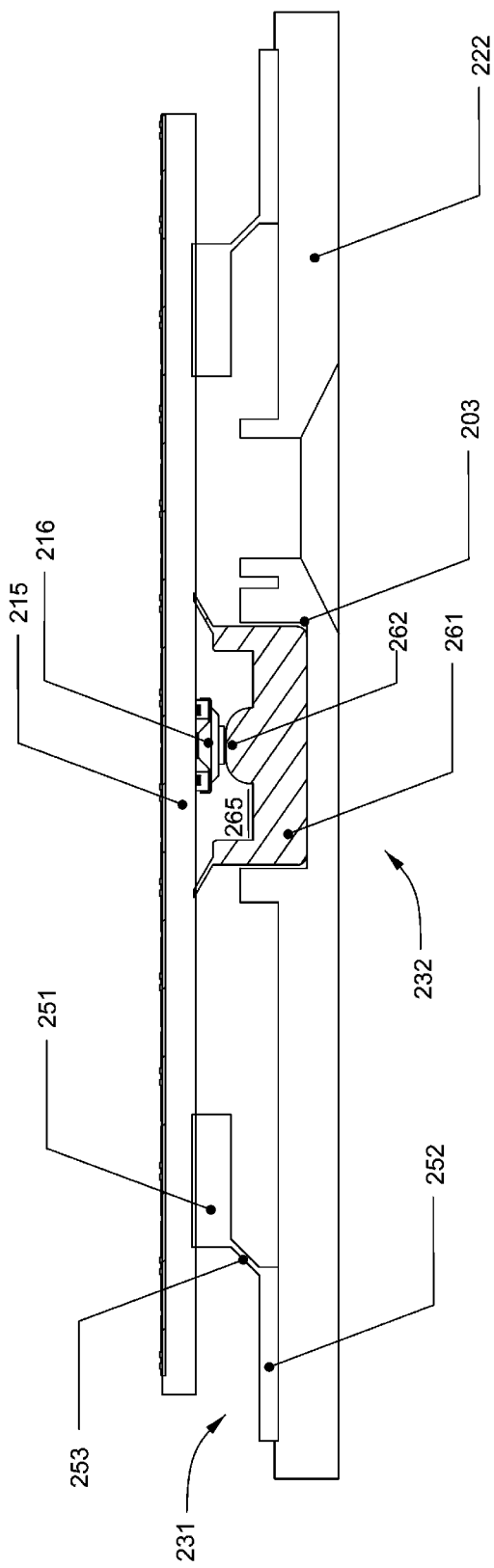
FIG. 8 is a sectional view of an elastic member in the sectional view shown in FIG. 7.

FIG. 3 shows a perspective view of a pressable touch panel 200 (labeled as 152 in FIG. 2) in the user interface 115 shown in FIG. 2 in a first direction (a forward direction). FIG. 4 shows a perspective view of the pressable touch panel 200 shown in FIG. 3 in a second direction (a reverse direction). FIG. 5 shows an exploded diagram of some embodiments of the pressable touch panel 200 shown in FIG. 3. FIG. 6 shows a bottom view of a circuit board 215 in the pressable touch panel 200 shown in FIG. 5. FIG. 7 shows a sectional view of the pressable touch panel 200 shown in FIG. 5 in an A-A' direction. FIG. 8 shows a sectional view of an elastic member in the sectional view shown in FIG. 7. Specifically, the A-A' direction is the z-axis direction defined in the present invention. In addition, in order to facilitate description and clearly show the specific structure of the elastic member, some components or members are omitted in FIG. 8.

As shown in FIGS. 3 to 8, the pressable touch panel 200 includes a touch assembly 210, an elastic assembly 230 and a housing 220.

The touch assembly 210 includes a first surface 205 for receiving a touch force, the elastic member 230 is arranged below the touch assembly 210, and the housing 220 is used to accommodate the elastic member 230, wherein the elastic member 230 is confined by the housing 220 to be in a compressed state to prevent liquid from passing through the elastic member 230.

Although the pressable touch panel in some embodiments of the present invention is arranged in a circular or annular shape, those skilled in the art should understand that the touch panel may also be arranged in a rectangular (cuboid) or elliptical (cylindroid) shape or any other suitable shape.

Specifically, taking the pressable touch panel 200 which is cylindrical as an example, the outer diameter of the elastic member 230 in a state where the elasticity is released is slightly greater than the inner diameter of the housing 220, so that the elastic member 230 can be arranged in the housing in a compressed manner. Similarly, if the pressable touch panel is arranged in a cuboid, the outer circumference of the elastic member 230 in a state where the elasticity is released is slightly greater than the inner circumference of the housing in a section along the first surface, so that the elastic member 230 can be arranged in the housing in a compressed manner.

Specifically, the touch force includes a touching force and a pressing force. The touching force includes a force generated in the first surface 205 (a plane where the x axis and the y axis are located), and the pressing force includes a force in the z-axis direction perpendicular to the first surface.

The elastic member 230 can provide a deformation space in the z-axis direction (i.e. a direction of the pressing force), and the elastic member is compressed in the z-axis direction when pressed, so that the touch assembly 210 moves from the first position to the second position in the z-axis direction under the pressing force. The elastic member 230 restores the touch assembly 210 from the second position to the first position under its own elastic action when the pressing force is released (or ended).

In some embodiments, the housing 220 includes a base 222 arranged below the elastic member 230 and a side portion 221 connected to the base 222, wherein the side portion 221 is used to confine the elastic member such that the elastic member is in a compressed state. Specifically, the side portion 221 is used to fix or mount the touch assembly 210 and the elastic member 230, and the base 222 is used to support the touch assembly 210 and the elastic member 230. In addition, the base 222 may include at least one radially extending mounting portion, and the mounting portion is provided with a through hole for fixing or mounting the pressable touch panel 200 into the ultrasound imaging system.

The side portion 221 is provided with a connecting member 201 mating with the base 222 to connect the base 222. The section of the side portion 221 may be annular, the connecting member 201 includes a hook which is arranged on a bottom surface of the side portion 221, and a recess mating with the hook is arranged on a bottom surface of the base 222 to connect the base 222 and the side portion 221. In some embodiments, the housing 220 may also be integrally formed. Specifically, the base 222 and the side portion 221 may be integrally formed.

In some embodiments, the touch assembly 210 includes a pressing board 211, a cover board 213 and a circuit board 215 sequentially arranged from top to bottom, and an upper surface of the pressing board 211 is the first surface 205. In some embodiments, in order to improve the user (for example, a sonographer) experience, the pressing board 211 is made of metal.

Although the pressing board 211 (the first surface of the pressable touch panel) is flat in some embodiments of the present invention, those skilled in the art should understand that the pressing board 211 may also be provided with a curved surface.

In some embodiments, a side edge of the cover board 213 includes at least two guide slots 202 arranged asymmetrically, and an inner side of the side portion 221 of the housing 220 is provided with guide protrusions (not shown) corresponding to the guide slots 202. Specifically, the guide slots 202 are arranged asymmetrically in the x-axis direction and/or the y-axis direction, which can prevent the pressable touch panel from being mounted in a wrong direction on the one hand, and prevent the touch assembly from rotating in the side portion of the housing (under the action of the touch force) on the other hand.

The touch assembly 210 further includes a first bonding sheet 212 arranged between the pressing board 211 and the cover board 213 and a second bonding sheet 214 arranged between the cover board 213 and the circuit board 215, wherein the first bonding sheet 212 and the second bonding sheet 214 may include a double-sided adhesive, a pressure sensitive adhesive (PSA), or other types of materials that can connect or bond any two boards together.

In some embodiments, as shown in FIG. 6, the touch assembly 210 further includes a switch member 216 and a connector 217 arranged on a lower surface of the circuit board 215, and the switch member 216 is used for triggering (or conducting) a touch signal (or a switch signal) under the action of the touch force and transmitting the touch signal to the circuit board 215 through the connector 217. Specifically, the switch member 216 includes a tact switch or a microswitch or other types of switches, and, by selecting an appropriate switch, the pressing function can be achieved under the action of a small force (e.g. about 0.5 N).

In some embodiments, as shown in FIG. 8, the elastic member 230 includes a cap-shaped body 231 including: a cap top 251 that contacts at least one of the circuit board 215 and the switch member 216, an outer edge portion 252 that contacts the base 222, and an inclined side portion 253 connected to the cap top 251 and the outer edge portion 252.

The arrangement of a cap-shaped structure can provide a function of stable elastic support on the one hand, and facilitates the user to perform pressing control at any position on the pressing board or the first surface on the other hand. For example, when the user presses an edge position of the pressing board, the structure of the cap-shaped body can facilitate the transmission of the pressing force to the switch member 216.

In some embodiments, the elastic member 230 is made of a rubber material or any other elastic material.

In some embodiments, the cap top 251 of the cap-shaped body 231 includes a first opening 255 (as shown in FIG. 5), the elastic member 230 further includes a bowl-shaped structure 232 arranged in the first opening 255, a protrusion 262 is arranged on a bottom surface 261 of the bowl-shaped structure 232 and contacts the switch member 216, and a space 265 is formed between an inner side surface of the bowl-shaped structure 232 and the protrusion 262. On the one hand, the arrangement of the bowl-shaped structure can facilitate the switch member to be triggered under the action of the pressing force. On the other hand, by arrangement of the protrusion 262, the switch member contacts and squeezes the protrusion under the pressing force to produce feedback sound, and the further arrangement of the space 265 can increase the feedback sound, thus giving the user feedback of successful pressing and improving the user experience. In addition, the function of pressing in the middle of the touch panel is also achieved by arrangement of the protrusion 262 and the protrusion 265.

In some embodiments, the base 222 is provided with a recess 203 for fixing the bowl-shaped structure 232. In addition, the base 222 is provided with a through hole 204 (as shown in FIG. 4) for fixing the connector 217.

In some embodiments, the base 222 is used to conduct the heat generated by a controller mounted below the touch panel 200 to the elastic member 230 so as to evaporate residual liquid on the elastic member 230. Specifically, the controller or the host computer of the ultrasound imaging system is arranged at a lower side of the touch panel, and the elastic member is arranged in a compressed manner to prevent liquid (for example, a disinfectant) from entering the controller or the host computer through the elastic member.

The controller or the host computer is equivalent to a heat source, which generates a large amount of heat during operation, and the heat is not needed by the ultrasound imaging system. Therefore, the ultrasound imaging system is generally provided with a heat dissipation device (for example, a fan) for heat dissipation. However, on the one hand, the pressable touch panel described in the present invention can allow the residual liquid on the elastic member to be evaporated as quickly as possible by use of the heat not needed by the system; and on the other hand, the gap between the touch assembly and the housing in the pressable touch panel is also more conducive to the heat dissipation of the host computer.

In some embodiments, the ultrasound imaging system includes a mounting housing (not shown) for arranging the touch panel 200, and the side portion 221 of the housing 220 of the touch panel 200 is provided with a sealing member 280 (as shown in FIG. 7) extending to the mounting housing to block and prevent liquid from entering the gap between the mounting housing and the side portion 221 of the housing 220 of the touch panel 200.

Figure 9:
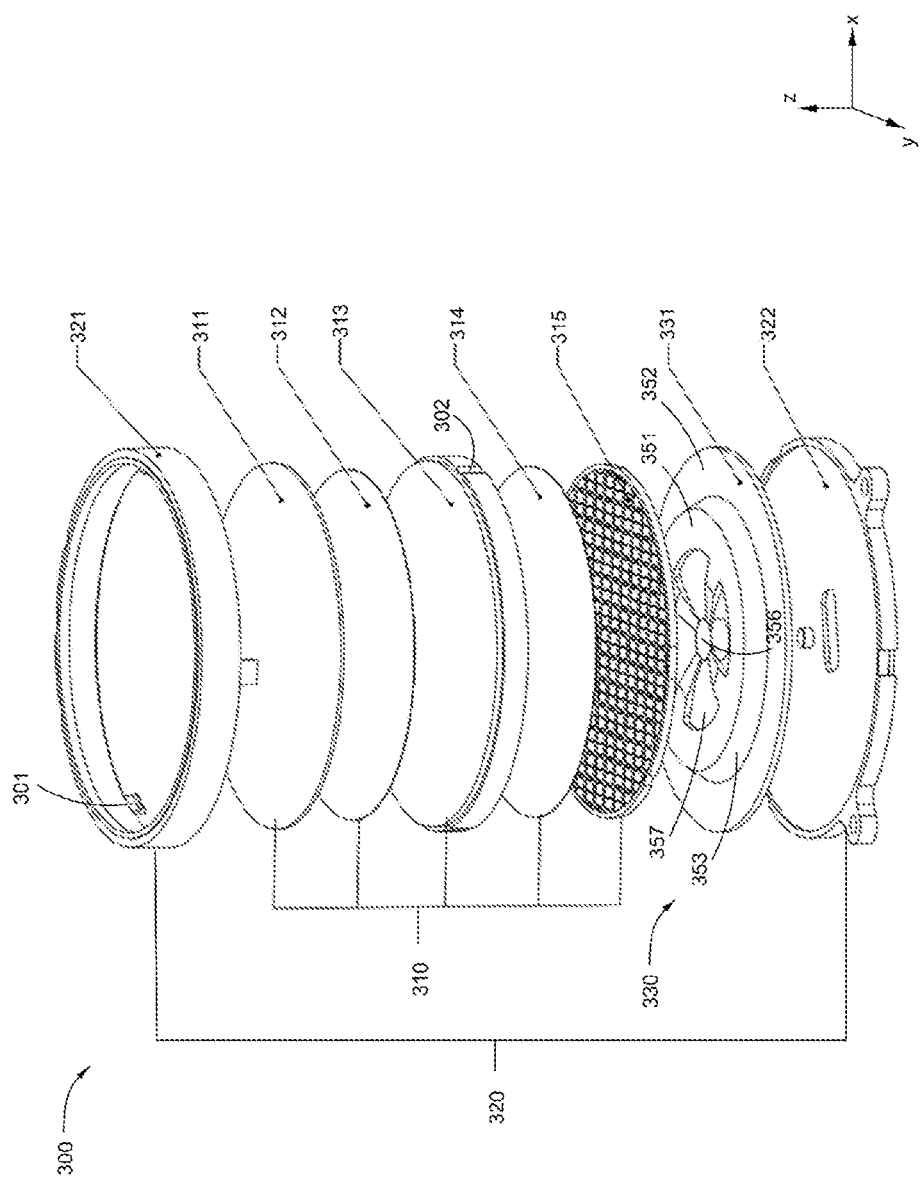
FIG. 9 is an exploded diagram of a pressable touch panel according to some other embodiments of the present invention.
Figure 10:
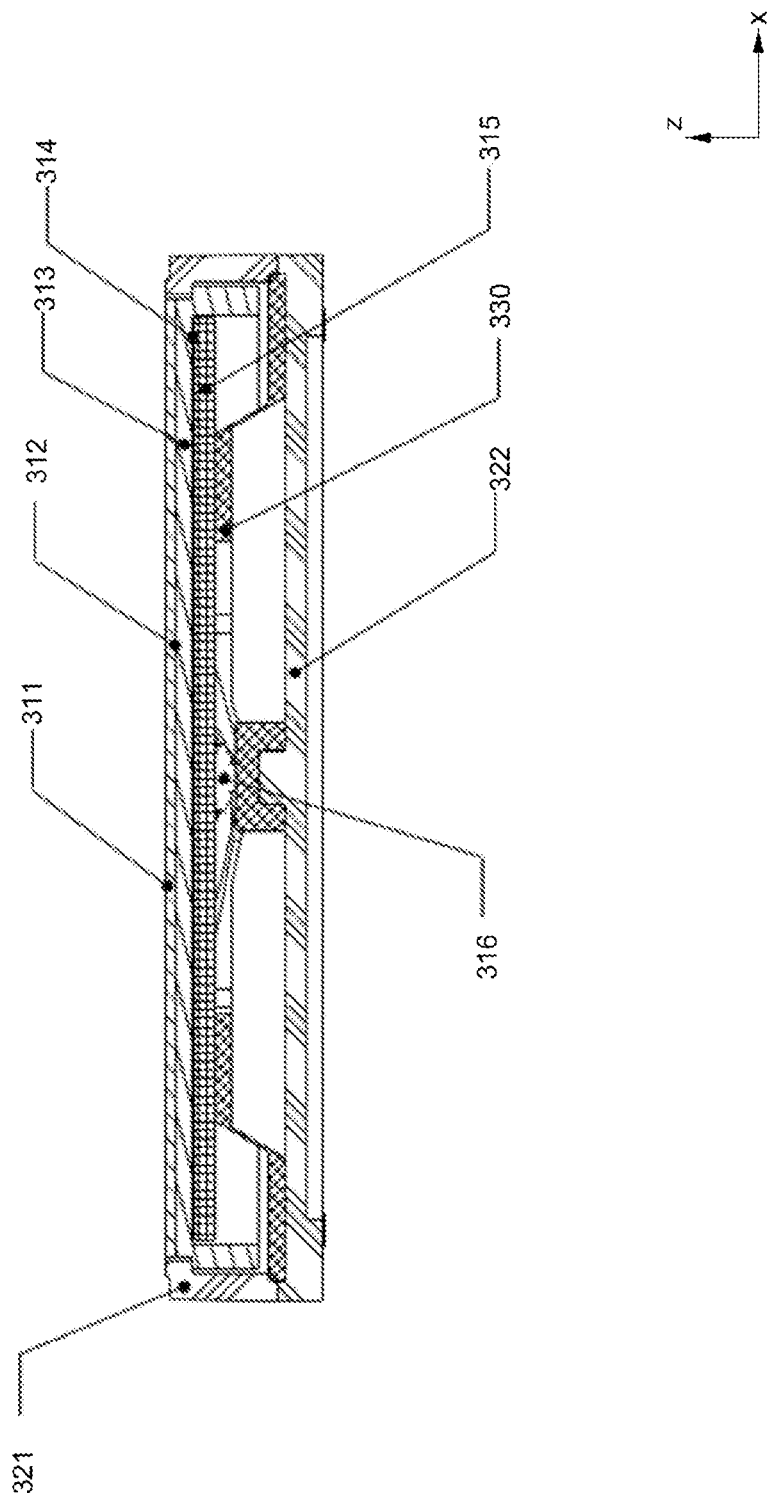
FIG. 10 is a sectional view of the pressable touch panel shown in FIG. 9 in an A-A' direction.

FIG. 9 shows an exploded diagram of a pressable touch panel 300 according to some other embodiments of the present invention. FIG. 10 shows a sectional view of the pressable touch panel 300 shown in FIG. 9 in an A-A' direction. Different from the pressable touch panel 200 of some embodiments shown in FIGS. 5 to 8, an elastic member 330 in the pressable touch panel 300 shown in FIGS. 9 to 10 is integrally formed.

Specifically, the elastic member 330 includes a cap-shaped body 331. The cap-shaped body 331 includes a cap top 351 that contacts at least one of a circuit board 315 and a switch member 316, an outer edge portion 352 that contacts a base 322, and an inclined side portion 353 connected to the cap top 351 and the outer edge portion 352. In some embodiments, at least one second opening 357 is arranged on a portion of the cap top 351 that does not contact the switch member 316. For example, as shown in FIG. 9, the portion that contacts the switch member 316 is defined as a central portion 356, and the cap top 351 is provided with at least one opening 357 around or near the central portion 356.

The pressable touch panel provided by the present invention not only has the pressing function, but also provides the function of pressing at any position of the pressing board through the arrangement of the cap-shaped body and the bowl-shaped structure in the elastic member, and solves the problem of liquid leakage upon disinfection of the ultrasound system by means of the compressible arrangement of the elastic member.

In addition, the arrangement of the protrusion and the space in the bowl-shaped structure in the elastic member not only increases the user's tactility, but also provides a feedback signal (for example, feedback sound) for the user's successful pressing, thus improving the user experience.

Furthermore, the pressable touch panel proposed by the present invention not only allows the liquid entering the touch panel to be evaporated as quickly as possible by use of the heat not needed by the ultrasound imaging system, but also further facilitates the heat dissipation of the host computer due to the gap between the touch assembly and the housing.

Some exemplary embodiments have been described above; however, it should be understood that various modifications can be made. For example, if the described techniques are performed in a different order and/or if the components of the described system, architecture, device, or circuit are combined in other manners and/or replaced or supplemented with additional components or equivalents thereof, a suitable result can be achieved. Accordingly, other implementations also fall within the protection scope of the claims.

The invention claimed is:

1. A pressable touch panel, comprising:
   a touch assembly comprising a first surface for receiving a touch force;
   an elastic member arranged below the touch assembly; and
   a housing for accommodating the elastic member,
   wherein the elastic member is confined by the housing to be in a compressed state to prevent liquid from passing through the elastic member,
   wherein the elastic member comprises a cap-shaped body comprising: a cap top that contacts at least one of a circuit board and a switch member; an outer edge portion that contacts a base; and an inclined side portion connected to the cap top and the outer edge portion;
   wherein the cap top of the cap-shaped body comprises a first opening, the elastic member further comprises a bowl-shaped structure arranged in the first opening, a protrusion is arranged on a bottom surface of the bowl-shaped structure and contacts the switch member, and a space is formed between an inner side surface of the bowl-shaped structure and the protrusion.

2. The pressable touch panel according to claim 1, wherein the housing comprises the base arranged below the elastic member and a side portion connected to the base, and the side portion is used to confine the elastic member such that the elastic member is in a compressed state.

3. The pressable touch panel according to claim 2, wherein the base is used to conduct the heat generated by a controller mounted below the touch panel to the elastic member so as to evaporate residual liquid on the elastic member.

4. The pressable touch panel according to claim 2, wherein an ultrasound imaging system comprises a mounting housing for arranging the touch panel, and the side portion of the housing of the touch panel is provided with a sealing member extending to the mounting housing to block and prevent liquid from entering a gap between the mounting housing and the side portion of the housing of the touch panel.

5. The pressable touch panel according to claim 2, wherein the side portion is provided with a connecting member mating with the base to connect the base.

6. The pressable touch panel according to claim 2, wherein the touch assembly comprises a pressing board, a cover board and the circuit board sequentially arranged from top to bottom, and an upper surface of the pressing board is the first surface.

7. The pressable touch panel according to claim 6, wherein the touch assembly further comprises a switch member and a connector arranged on a lower surface of the circuit board, and the switch member is used to transmit a touch signal to the circuit board through the connector under the action of the touch force.

8. The pressable touch panel according to claim 1, wherein at least one second opening is arranged on a portion of the cap top that does not contact the switch member.

9. An ultrasound imaging system, comprising the pressable touch panel according to claim 1.

* * * * *